(12) United States Patent
Ni et al.

(10) Patent No.: US 11,225,443 B2
(45) Date of Patent: Jan. 18, 2022

(54) METHOD FOR DIRECTLY PREPARING P-XYLENE FROM SYNTHETIC GAS AND AROMATIC HYDROCARBON

(71) Applicant: DALIAN INSTITUTE OF CHEMICAL PHYSICS, CHINESE ACADEMY OF SCIENCES, Dalian (CN)

(72) Inventors: Youming Ni, Dalian (CN); Wenliang Zhu, Dalian (CN); Zhongmin Liu, Dalian (CN); Yong Liu, Dalian (CN); Zhiyang Chen, Dalian (CN); Hongchao Liu, Dalian (CN); Xiangang Ma, Dalian (CN); Shiping Liu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 85 days.

(21) Appl. No.: 16/763,015

(22) PCT Filed: Nov. 21, 2017

(86) PCT No.: PCT/CN2017/112109
§ 371 (c)(1),
(2) Date: May 11, 2020

(87) PCT Pub. No.: WO2019/095404
PCT Pub. Date: May 23, 2019

(65) Prior Publication Data
US 2020/0270188 A1 Aug. 27, 2020

(30) Foreign Application Priority Data
Nov. 15, 2017 (CN) .......................... 201711133301.1

(51) Int. Cl.
*C07C 2/86* (2006.01)
*B01J 21/18* (2006.01)
(Continued)

(52) U.S. Cl.
CPC ................ *C07C 2/862* (2013.01); *B01J 21/18* (2013.01); *B01J 29/405* (2013.01); *B01J 29/46* (2013.01);
(Continued)

(58) Field of Classification Search
CPC ....... C07C 2/86; C07C 2/862; C07C 2529/40; C07C 2529/46; C07C 1/04; C07C 4/00;
(Continued)

(56) References Cited

U.S. PATENT DOCUMENTS 4,487,984 A 12/1984 Imai
4,975,402 A * 12/1990 Le Van Mao ............ B01J 29/40
502/68

(Continued)

FOREIGN PATENT DOCUMENTS

CN 104945219 A 9/2015
RU 2119470 C1 9/1998
(Continued)

OTHER PUBLICATIONS

International Search Report dated Aug. 24, 2018 in corresponding International application No. PCT/CN2017/112109; 4 pages.
(Continued)

*Primary Examiner* — In Suk C Bullock
*Assistant Examiner* — Jason Y Chong
(74) *Attorney, Agent, or Firm* — Maier & Maier, PLLC

(57) ABSTRACT

A method for directly preparing p-xylene from synthetic gas and aromatic hydrocarbon. The method includes contacting the feedstock containing synthetic gas and aromatic hydrocarbon excluding p-xylene with the catalyst in the reaction (Continued)

zone under reaction conditions sufficient to convert at least part of the feedstock to obtain a reaction effluent containing p-xylene; and separating p-xylene from the reaction effluent, where the catalyst includes a highly dispersed metal oxide material confined by an inert carrier, an acidic molecular sieve, and optionally at least one of graphite powder and dispersant, where in the highly dispersed metal oxide material confined by the inert carrier, the inert carrier is at least one of silicon oxide and alumina, and the content of the metal oxide in terms of metal is less than or equal to 10% by mass calculated based on the weight of the highly dispersed metal oxide material confined by the inert carrier.

13 Claims, 2 Drawing Sheets

(51) Int. Cl.

| | | |
|---|---|---|
| *B01J 29/40* | (2006.01) | |
| *B01J 29/46* | (2006.01) | |
| *B01J 29/48* | (2006.01) | |
| *B01J 35/02* | (2006.01) | |
| *B01J 37/00* | (2006.01) | |
| *B01J 37/02* | (2006.01) | |
| *B01J 37/03* | (2006.01) | |
| *B01J 37/04* | (2006.01) | |
| *B01J 37/06* | (2006.01) | |
| *B01J 37/08* | (2006.01) | |

(52) U.S. Cl.
CPC ............. *B01J 29/48* (2013.01); *B01J 35/023* (2013.01); *B01J 35/026* (2013.01); *B01J 37/0009* (2013.01); *B01J 37/0236* (2013.01); *B01J 37/031* (2013.01); *B01J 37/036* (2013.01); *B01J 37/04* (2013.01); *B01J 37/06* (2013.01); *B01J 37/088* (2013.01); *C07C 2529/40* (2013.01); *C07C 2529/46* (2013.01)

(58) Field of Classification Search
CPC .. C07C 5/22; C07C 15/08; B01J 21/18; B01J 29/40; B01J 29/405; B01J 29/46; B01J 29/48; B01J 35/023; B01J 35/026; B01J 35/10; B01J 37/0009; B01J 37/0236; B01J 37/031; B01J 37/036; B01J 37/04; B01J 37/06; B01J 37/088; Y02P 20/52
See application file for complete search history.

(56) References Cited

U.S. PATENT DOCUMENTS

| | | | |
|---|---|---|---|
| 6,459,006 | B1 | 10/2002 | Ou et al. |
| 2004/0097769 | A1 | 5/2004 | Ou et al. |

FOREIGN PATENT DOCUMENTS

| | | |
|---|---|---|
| WO | 0069796 A1 | 11/2000 |
| WO | 2004/043593 A | 5/2004 |

OTHER PUBLICATIONS

Extended European Search Report dated Dec. 11, 2020, in connection with corresponding EP Application No. 17932310.0; 7 pages.

\* cited by examiner

METHOD FOR DIRECTLY PREPARING P-XYLENE FROM SYNTHETIC GAS AND AROMATIC HYDROCARBON

FIELD

The present invention refers to a method for directly preparing p-xylene from synthetic gas and aromatic hydrocarbon.

BACKGROUND

P-xylene (PX) is an important basic chemical raw material, mainly used to prepare p-dibenzoic acid (PTA), and p-dibenzoic acid is used to produce polyethylene terephthalate (PET). At present, p-xylene is mainly obtained from aromatics complex plant, in which high-purity PX products are obtained from naphtha through reforming, aromatics extraction, aromatics fractionation, disproportionation and transalkylation, isomerization of xylene and adsorption separation. The proportion of p-xylene in three kinds of xylenes is less than 25% because of thermodynamic limitation, and the material recycling throughput is high, the energy consumption is high, and the investment is high. The alkylation of toluene with methanol to produce p-xylene can break through the thermodynamic limitation and a high proportion of p-xylene can be obtained, which is a promising production route for PX.

As everyone knows, methanol is generally produced using synthetic gas as a raw material. If the synthetic gas is reacted with toluene to prepare p-xylene directly, advantages of shortening reaction path, saving energy consumption, reducing sewage discharge and fixed investment can be realized by this method.

WO2004/043593 discloses a method for selectively producing p-xylene by reacting an aromatic hydrocarbon with a feed containing carbon monoxide and hydrogen in the presence of a selectively activated catalyst and a catalyst used in the method, the catalyst comprises an acid silicate-based material and a metal or metal oxide with catalytic activity.

Chinese patent application CN104945219A discloses a method for preparing toluene and p-xylene in one step with benzene and synthetic gas and a catalyst used therein, in which the catalyst comprises a metal oxide component and a solid acid component.

U.S. Pat. No. 4,487,984 discloses a method for preparing alkyl aromatic compounds by reacting aromatic compounds with synthetic gas in the presence of a bifunctional catalyst under alkylation conditions, in which the bifunctional catalyst comprises composite oxide of copper, zinc, and aluminum or chromium and aluminosilicate.

There is still a need to develop a new method for directly preparing p-xylene from synthetic gas and aromatic hydrocarbon that can achieve a high raw material conversion rate and a high selectivity to p-xylene and is environmentally friendly.

SUMMARY

In order to overcome the problems in the prior art, the inventors conducted diligent research. It was found that a catalyst containing a highly dispersed metal oxide material confined by an inert carrier, an acidic molecular sieve, and optionally at least one of graphite powder and dispersant is very suitable for the direct preparation of p-xylene from synthetic gas and aromatic hydrocarbon. The method for directly preparing p-xylene from synthetic gas and aromatic hydrocarbonusing the catalyst can achieve a high raw material conversion rate and a high selectivity to p-xylene, and is environmentally friendly. The present invention has been completed based on the above findings.

Therefore, an object of the present invention is to provide a method for directly preparing p-xylene from synthetic gas and aromatic hydrocarbon, the method comprising:

Contacting the feedstock containing synthetic gas and aromatic hydrocarbon excluding p-xylene with the catalyst in the reaction zone under reaction conditions sufficient to convert at least part of the feedstock to obtain a reaction effluent containing p-xylene; and Separating p-xylene from the reaction effluent, Wherein the catalyst comprises a highly dispersed metal oxide material confined by an inert carrier, an acidic molecular sieve, and optionally at least one of graphite powder and dispersant, wherein in the highly dispersed metal oxide material confined by the inert carrier, the inert carrier is at least one of silicon oxide and alumina, and the content of the metal oxide in terms of metal is less than or equal to 10% by mass calculate based on the weight of the highly dispersed metal oxide material confined by the inert carrier, and wherein the acidic molecular sieve is one selected from a group consisting of modified acidic ZSM-5 molecular sieve, modified acidic ZSM-11 molecular sieve and mixtures thereof.

In one embodiment, the reaction zone comprises a fixed bed reactor, or multiple fixed bed reactors in series and/or parallel.

In one embodiment, the reaction conditions comprise: a reaction temperature in a range of 300-450° C., a reaction pressure in a range of 0.5-10.0 MPa, a molar ratio of hydrogen to carbon monoxide in the synthetic gas in a range of 1:9-9:1, a weight hourly space velocity of aromatic hydrocarbon in a range of 0.01-20 $h^{-1}$, and a volume hourly space velocity of synthetic gas in the standard state in a range of 1000-20000 $h^{-1}$.

DESCRIPTION OF PREFERRED EMBODIMENTS

In a first aspect, the present invention provides a method for directly preparing p-xylene from synthetic gas and aromatic hydrocarbon, the method including:

Contacting the feedstock containing synthetic gas and aromatic hydrocarbon excluding p-xylene with the catalyst in the reaction zone under reaction conditions sufficient to convert at least part of the feedstock to obtain a reaction effluent containing p-xylene; and Separating p-xylene from the reaction effluent, Wherein the catalyst comprises a highly dispersed metal oxide material confined by an inert carrier, an acidic molecular sieve, and optionally at least one of graphite powder and dispersant, wherein in the highly dispersed metal oxide material confined by the inert carrier, the inert carrier is at least one of silicon oxide and alumina, and the content of the metal oxide in terms of metal is less than or equal to 10% by mass calculated based on the weight of the highly dispersed metal oxide material confined by the inert carrier, and wherein the acidic molecular sieve is one selected from a group consisting of modified acidic ZSM-5 molecular sieve, modified acidic ZSM-11 molecular sieve and mixtures thereof.

Catalyst for Preparing p-xylene

As described above, the catalyst used in the method of the present invention comprises a highly dispersed metal oxide material confined by an inert carrier, an acidic molecular sieve, and optionally at least one of graphite powder and dispersant, wherein in the highly dispersed metal oxide material confined by the inert carrier, the inert carrier is at least one of silicon oxide and alumina, and the content of the metal oxide in terms of metal is less than or equal to 10% by mass calculate based on the weight of the highly dispersed metal oxide material confined by the inert carrier, and wherein the acidic molecular sieve is one selected from a group consisting of modified acidic ZSM-5 molecular sieve, modified acidic ZSM-11 molecular sieve and mixtures thereof.

In one embodiment, the metal oxide in the highly dispersed metal oxide material confined by the inert carrier is an oxide of at least one of metals excluding aluminum and radioactive elements. Preferably, the metal oxide in the highly dispersed metal oxide material confined by the inert carrier is an oxide of at least one of zinc, chromium, zirconium, copper, manganese, platinum and palladium. More preferably, the metal oxide in the highly dispersed metal oxide material confined by the inert carrier is an oxide of at least one of zinc, chromium, and zirconium.

In one embodiment, the content of the metal oxide in terms of metal in the highly dispersed metal oxide material confined by the inert carrier is less than or equal to 10% by weight; preferably less than or equal to 5% by weight; more preferably less than or equal to 2% by weight calculated based on the weight of the highly dispersed metal oxide material confined by the inert carrier. Unless otherwise indicated, the term "the content of the metal oxide" as used herein does not include the content of alumina, if alumina is present.

In one embodiment, the average particle size of the metal oxide in the highly dispersed metal oxide material confined by the inert carrier is less than or equal to 100 nm, preferably less than or equal to 50 nm, and more preferably less than or equal to 20 nm.

In a preferred embodiment, the characteristic diffraction peaks of the metal oxide are not present in the X-ray powder diffraction pattern of the highly dispersed metal oxide material confined by the inert carrier.

The highly dispersed metal oxide material confined by the inert carrier is different from the conventional metal composite oxide materials known in the art. For example, the highly dispersed metal oxide material confined by the inert carrier has a high dispersion of metal oxide (no characteristic XRD diffraction peak of metal oxide), a small mass fraction of metal oxide (generally less than 10%) and a small average particle size of metal oxide (generally less than 100 nm), and usually has a large specific surface area (generally greater than 400m$^2$/g). Conventional composite metal oxide materials are known in the art as copper-zinc-aluminum composite oxide materials (CuZnAlO$_x$) for low-temperature methanol synthesis, zinc-chromium-aluminum composite oxide materials (ZnCrAlO$_x$) and zinc-zirconium composite oxide materials (ZnZrO$_x$) for high-temperature methanol synthesis and have a mass fraction of metal oxide generally greater than 80%, a significant characteristic XRD diffraction peaks of the metal oxide, and a specific surface area generally lower than 100 m$^2$/g. Without undesirably being limited to any particular theory, it is believed that a large amount of the inert carrier present in the highly dispersed metal oxide material confined by the inert carrier in the present invention can provide a large specific surface area and can not only provide a large specific surface area, but also stabilize the metal oxide used as a catalytically active component due to the confinement effect.

In one embodiment, the average particle diameter of the highly dispersed metal oxide material confined by the inert carrier is less than or equal to 5 mm, preferably less than or equal to 1 mm, more preferably less than or equal to 0.5 mm, still more preferably less than or equal to 0.1 mm, still more preferably less than or equal to 0.05 mm In some embodiments, the highly dispersed metal oxide material confined by the inert carrier can be prepared by a coprecipitation-calcination method. For example, in the case of using alumina as a carrier, the highly dispersed metal oxide material confined by the inert carrier can be prepared as follows: formulating a mixed metal salt aqueous solution from a catalytically active metal salt and an aluminum salt; contacting the mixed metal salt aqueous solution with the precipitant aqueous solution to co-precipitate the metal ions in the mixed metal salt aqueous solution; aging; and washing, drying and then calcining the precipitate. Examples of the precipitant comprise but are not limited to sodium carbonate, potassium carbonate, ammonium carbonate, sodium bicarbonate, potassium bicarbonate, ammonium bicarbonate, ammonia water, sodium hydroxide, potassium hydroxide, and mixtures thereof.

In one embodiment, the temperature during the coprecipitation is in a range of 0° C. to 90° C., the pH during the coprecipitation is in a range of 7.0 to 8.5, the aging time is not less than 1 hour, and the calcination temperature is in a range of 300° C. to 700° C.

In a specific embodiment, the highly dispersed metal oxide material confined by the inert carrier is prepared as follows: formulating an mixed metal salt aqueous solution with a total metal ion concentration in a range of 0.1 mol/L to 3.5 mol/L from a catalytically active metal salt and an aluminum salt; then contacting the mixed metal salt aqueous solution with the precipitant aqueous solution with a molar concentration in a range of 0.1 mol/L to 3.5 mol/L at a temperature in a range of 0° C. to 90° C. under stirring to co-precipitate the metal ions in the metal salt; and then aging for a period of time, the pH value of the solution during the co-precipitation process can be in a range of 7.0 to 8.5, and the aging time is not less than 1 hour; after filtering and washing the resulting precipitate, it is calcined at a temperature for example in a range of 300° C. to 700° C. to prepare a highly dispersed metal oxide materials confined by an inert carrier.

There is no particular limitation on the kinds of the aluminum salt and the catalytically active metal salt as long as they are water-soluble, for example, with a water solubility of more than 1 g/L at 25° C. Examples of the aluminum salt and the catalytically active metal salt comprise, but are not limited to, hydrochloride, sulfate, and nitrate.

There is no particular limitation on the method for contacting the mixed metal salt aqueous solution with the precipitant aqueous solution. In a specific embodiment, the contacting can be accomplished by co-current feeding, forward feeding or reverse feeding.

In other embodiments, the highly dispersed metal oxide material confined by the inert carrier can be prepared by a sol-gel method. For example, in the case where at least silica is used as a carrier, the highly dispersed metal oxide material confined by the inert carrier can be prepared as follows: adding an aqueous solution of a catalytically active metal salt and an aqueous solution of a precipitant together into siloxane-based compound, so that a co-precipitation and sol-gel reaction can be carried out, and then washing, drying and then calcining the obtained gel to prepare the highly dispersed metal oxide material confined by the inert carrier.

Examples of the precipitant comprise but are not limited to one or more of ammonium carbonate, ammonia water, ammonium bicarbonate, ammonium dihydrogen carbonate, and urea.

In one embodiment, the siloxane-based compound is an alkyl orthosilicate, and examples of alkyl orthosilicate comprise, but are not limited to, methyl orthosilicate, ethyl orthosilicate, n-propyl orthosilicate, isopropyl silicate, n-butyl orthosilicate, isobutyl orthosilicate, t-butyl orthosilicate and mixtures thereof.

The acidic molecular sieve component in the catalyst of the present invention is one selected from a group including modified acidic ZSM-5 molecular sieve, modified acidic ZSM-11 molecular sieve and mixtures thereof.

In some embodiments, the modification of the acidic molecular sieve is one or more of modification by phosphorus, modification by boron, modification by silicon, modification by alkaline earth metal, and modification by rare earth metal.

In some embodiments, the atomic ratio of silicon to aluminum in the acidic ZSM-5 and ZSM-11 molecular sieves is Si/Al=3 to 200, preferably Si/Al=100 to 150.

In some embodiments, the crystals of the acidic ZSM-5 and ZSM-11 molecular sieves have a scale in micrometer or nanometer, and the crystals contain a microporous structure or a mesoporous-microporous structure. The modified acidic molecular sieve is commercially available or can be prepared by essentially known methods. There is no particular limitation on the specific method for preparing the modified acidic molecular sieve. For example, the modified acidic molecular sieve can be obtained by modifying the commercially available acidic ZSM-5 molecular sieve or acidic ZSM-11 molecular sieve.

In a specific embodiment, the acidic molecular sieve can be impregnated in, for example, $H_3PO_4$ $NH_4H_2PO_4$ or $(NH_4)_2HPO_4$ aqueous solution, and then the impregnated acidic molecular sieve is dried and then calcined to obtain a phosphorus-modified acidic molecular sieve with a phosphorus content in a range of 0.5% to 10% by weight calculated based on the weight of the modified molecular sieve.

In another specific embodiment, the acidic molecular sieve can be impregnated in, for example, an aqueous solution of $H_3BO_3$ and then the impregnated acidic molecular sieve is dried and then calcined to obtain a boron modified acidic molecular sieve with a boron content in a range of 0.5% to 10% by weight calculated based on the weight of the modified molecular sieve.

In yet another specific embodiment, a silicon-modified acidic molecular sieve can be prepared by treatment with a siloxane compound by a liquid-phase deposition method and/or treatment with a silane compound by a vapor-phase deposition method. The siloxane compounds and silane compounds that can be used are represented by the following structural formulas:

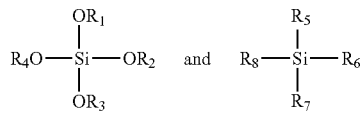

Wherein $R_1$, $R_2$, $R_3$, $R_4$, $R_5$, $R_6$, $R_7$ and $R_8$ are each independently selected from $C_1$-$C_{10}$ alkyl. An example of the siloxane compound is ethyl orthosilicate, and an example of the silane compound is tetramethylsilane.

In a specific embodiment, the liquid-phase deposition method is performed as follows: the siloxane compound is dissolved in an inert organic solvent to provide a siloxane compound solution, and then an acidic molecular sieve is soaked or impregnated with the siloxane compound solution, dried and then calcined to obtain a silicon-modified acidic molecular sieve. Based on the weight of the modified molecular sieve, the loading capacity of silicon in the silicon-modified acidic molecular sieve may be 0.5 to 10.0% by weight, and the loading capacity of silicon does not include the original silicon in the acidic molecular sieve. The inert organic solvent may be any solvent that does not react with the siloxane compound and molecular sieve, such as n-hexane, cyclohexane, and n-heptane.

In a specific embodiment, the vapor deposition method is performed as follows: a silane compound gas is passed through an acidic molecular sieve, and then the treated acidic molecular sieve is calcined to obtain a silicon-modified acidic molecular sieve. Based on the weight of the modified molecular sieve, the loading capacity of silicon in the silicon-modified acidic molecular sieve may be 0.5 to 10.0% by weight, and the loading capacity of silicon does not include the original silicon in the acidic molecular sieve.

In a specific embodiment, the acidic molecular sieve can be impregnated with an aqueous solution of alkaline earth metal salt or rare earth metal salt, and then the impregnated acidic molecular sieve can be filtered, dried and calcined to obtain an alkaline earth metal or rare earth metal modified acidic molecular sieve with an alkaline earth metal or rare earth metal content in a range of 0.5% to 10% by weight calculated based on the weight of the modified molecular sieve.

In one embodiment, the average particle size of the acidic molecular sieve is less than or equal to 5 mm, preferably less than or equal to 0.5 mm, more preferably less than or equal to 0.1 mm, still more preferably less than or equal to 0.05 mm In some embodiments, the dispersant is one selected from alumina, silica, and mixtures thereof. There is no particular limitation on alumina, silica or alumina-silica that can be used as a dispersant, and they are commercially available from many suppliers.

There is no particular limitation on the graphite powder that can be used in the present invention, and they are commercially available from many suppliers. In some embodiments, the graphite powder has an average particle size in a range of 0.05 to 5 microns.

In one embodiment, the catalyst used in the method of the present invention can be prepared by a method comprising the following steps:

(1) Providing a highly dispersed metal oxide material confined by the inert carrier;

(2) Providing a modified acidic molecular sieve;

(3) Mixing the highly dispersed metal oxide material confined by the inert carrier obtained in step (1) with the modified acidic molecular sieve obtained in step (2) and optionally at least one of graphite powder and dispersant to obtain a mixture, and molding the resulted mixture.

In some embodiments, the catalyst of the present invention comprises a highly dispersed metal oxide material confined by an inert carrier in an amount ranging from 10% to 90% by weight. The lower limit of the content of the highly dispersed metal oxide material confined by the inert carrier may be 12%, 15%, 18%, 20%, 22%, 25%, 28%, 30%, 32%, 35%, 38%, 40%, 42%, 45%, 48%, or 50% by weight, and the upper limit may be 88%, 85%, 82%, 80%, 78%, 75%, 72%, 70%, 68%, 65%, 62%, 60%, 58%, 55%, 52% or 50% by weight, calculated based on the weight of the catalyst.

In some embodiments, the catalyst of the present invention comprises an acidic molecular sieve in an amount ranging from 10% to 90% by weight. The lower limit of the content of the acidic molecular sieve may be 12%, 15%, 18%, 20%, 22%, 25%, 28%, 30%, 32%, 35%, 38%, 40%, 42%, 45%, 48%, or 50% by weight, and the upper limit may be 88%, 85%, 82%, 80%, 78%, 75%, 72%, 70%, 68%, 65%, 62%, 60%, 58%, 55%, 52%, or 50% by weight, calculated based on the weight of the catalyst.

In some embodiments, the catalyst of the present invention comprises a graphite powder in an amount ranging from 0% to 10% by weight, for example, ranging from 0 to 8 wt %, from 0 to 7 wt %, from 0 to 6 wt %, or from 0 to 5 wt %, calculated based on the weight of the catalyst.

In some embodiments, the catalyst of the present invention comprises a dispersant in an amount ranging from 0% to 40% by weight, for example, ranging from 0 to 38 wt %, from 0 to 35 wt %, from 0 to 30 wt %, or from 0 to 25 wt %, calculated based on the weight of the catalyst.

In some embodiments, the catalyst of the present invention comprises a highly dispersed metal oxide material confined by an inert carrier in an amount ranging from 10% to 90% by weight, an acidic molecular sieve in an amount ranging from 10% to 90% by weight, a graphite powder in an amount ranging from 0% to 10% by weight and a dispersant in an amount ranging from 0% to 40% by weight, wherein the total content of the highly dispersed metal oxide material confined by the inert carrier and the acidic molecular sieve is in a range of 60% to 100% by weight, and the weight percentage is calculated based on the total weight of the catalyst. In some preferred embodiments, the catalyst of the present invention comprises a highly dispersed metal oxide material confined by an inert carrier in an amount ranging from 20% to 80% by weight, an acidic molecular sieve in an amount ranging from 20% to 80% by weight, a graphite powder in an amount ranging from 0% to 3% by weight and a dispersant in an amount ranging from 0% to 30% by weight, and the weight percentage is calculated based on the total weight of the catalyst.

There is no particular limitation on the shape of the catalyst, only that it is suitable for the intended application process. In a specific embodiment, the particle shape of the catalyst may be spherical, bar-shaped, cylindrical, semi-cylindrical, prismatic, clover-shaped, ring-shaped, pellet-shaped, regular or irregular particle-shape or flake.

In the present invention, the terms "powder", "particles" and "powdered particles" are used interchangeably.

Method for preparing p-xylene from synthetic gas and aromatic hydrocarbon

As mentioned above, in the method of the present invention, contacting the feedstock containing synthetic gas and aromatic hydrocarbon excluding p-xylene with the catalyst in the reaction zone is under reaction conditions that sufficient to convert at least part of the feedstock to obtain a reaction effluent containing p-xylene.

In the method of the present invention, synthetic gas is used as one of the raw materials. As used herein, the term "synthetic gas" refers to a mixture of hydrogen and carbon monoxide. In the raw material of the synthetic gas, the molar ratio of hydrogen to carbon monoxide may be in a range of 1:9 to 9:1, preferably in a range of 1:9 to 1:1.

In the method of the present invention, aromatic hydrocarbon excluding p-xylene is also used as one of the raw materials. In one embodiment, the aromatic hydrocarbon excluding p-xylene is at least one aromatic hydrocarbon having the following general formula:

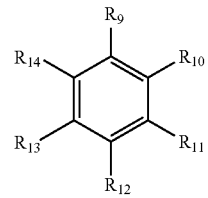

Wherein, $R_9$, $R_{10}$, $R_{11}$, $R_{12}$, R13 and $R_{14}$ are each independently selected from hydrogen, or a $C_1$-$C_{10}$ hydrocarbyl, preferably a $C_1$-$C_6$ hydrocarbyl, such as methyl, ethyl, propyl, isopropyl or phenyl.

Examples of the aromatic hydrocarbon raw material that can be used in the method of the present invention comprise, but are not limited to: benzene, toluene, ethylbenzene, m-xylene, o-xylene, cumene, sym-trimethylbenzene, sym-tetramethylbenzene, biphenyl, and mixtures thereof. In a preferred embodiment, the aromatic hydrocarbon raw material comprises toluene. In the method of the present invention, the reaction zone may be one or more fixed bed reactors. The fixed bed reactor can be operated in continuous mode. When a plurality of fixed bed reactors are used, the plurality of reactors may be configured in series, parallel, or a combination of series and parallel.

In the method of the present invention, the reaction conditions include: a reaction temperature in a range of 300-450° C., a reaction pressure in a range of 0.5-10.0 MPa, a molar ratio of hydrogen to carbon monoxide in the synthetic gas in a range of 1:9-9:1, a weight hourly space velocity of aromatic hydrocarbon in a range of 0.01-20 $h^{-1}$, and a volume hourly space velocity of synthetic gas in the standard state in a range of 1000-20000 $h^{-1}$.

In a preferred embodiment, the reaction conditions include: a reaction temperature in a range of 320-400° C., a molar ratio of hydrogen to carbon monoxide in the synthetic gas in a range of 1:9-1:1, a reaction pressure in a range of 5.0-10.0 MPa, a weight hourly space velocity of aromatic hydrocarbon in a range of 0.5-3$h^{-1}$, and a volume hourly space velocity of synthetic gas in the standard state in a range of 1000-4000 $h^{-1}$.

Without undesirably being limited to any specific theory, it is believed that the reaction process for preparing p-xylene by reacting synthetic gas with aromatic hydrocarbon is very complicated and includes a series of reaction processes, such as:

1) a reaction for directly preparing aromatic hydrocarbon from synthetic gas (take directly preparing toluene as an example)

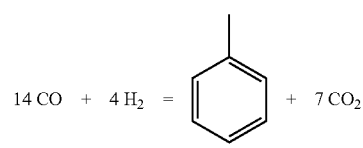

2) an alkylation reaction of synthetic gas with aromatic hydrocarbon (take alkylation reaction of synthetic gas with toluene as an example)

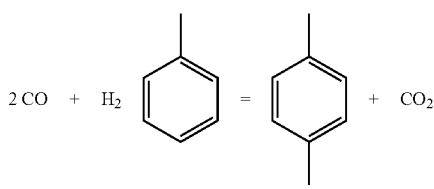

3) transalkylation reaction (for example, preparing p-xylene from m-xylene and preparing p-xylene from sym-trimethylbenzene and benzene)

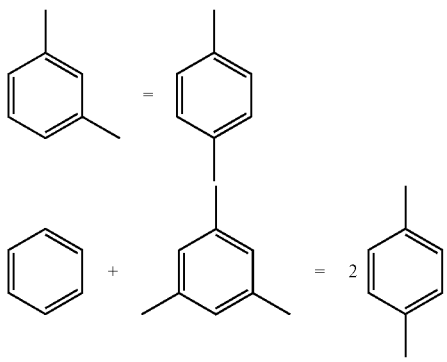

Oxygen atoms in CO mainly enter into $CO_2$, so little waste water is produced during the reaction.

Separation of Reaction Effluent

In the method of the present invention, the separation of the p-xylene product from the reaction effluent containing p-xylene may be accomplished according to essentially known methods.

The beneficial effects of the present invention includes: compared with the method for preparing p-xylene by the alkylation reaction of methanol and p-toluene, the method of the present invention has advantages of a long catalyst life, less waste water, low raw material cost, a wide range of raw material sources, and low energy consumption. Compared with conventional metal composite oxide materials, the highly dispersed metal oxide material confined by the inert carrier used in the method of the present invention has advantages of a large specific surface, high catalytic activity, and low content of relatively expensive active metal oxide components, less heavy metal ion emissions during preparing process and more easier to shaped into industrial catalyst.

DETAILED DESCRIPTION

The present invention will be described in detail below with reference to examples, but the present invention is not limited to these examples.

Unless otherwise specified, the raw materials in the embodiments of the present invention are purchased through commercial ways.

In the examples, two Agilent 7890 gas chromatographs with a gas autosampler, a TCD detector connected to a TDX-1 packed column, and a FID detector connected to a FFAP and PLOT-Q capillary column are used for automatic gas composition analysis.

In the examples, conversion rate and selectivity are calculated based on the number of moles of carbon:

Conversion rate of carbon monoxide=[(the number of moles of carbon in carbon monoxide in the feed)−(the number of moles of carbon in carbon monoxide in the discharge)]÷(the number of moles of carbon in carbon monoxide in the feed)×100%

Conversion rate of toluene=[(the number of moles of carbon in toluene in the feed)−(the number of moles of carbon in toluene in the discharge)]÷(the number of moles of carbon in toluene in the feed)×100%;

Selectivity to xylene=(the number of moles of carbon in xylene in the discharge)÷(the number of moles of carbon in all hydrocarbon products in the discharge−the number of moles of carbon in raw material of toluene)×100%

Proportion of p-xylene=(the number of moles of carbon in p-xylene in the discharge)÷(the number of moles of carbon in all xylene in the discharge)×100%

When the raw material is other aromatic hydrocarbon, the calculation method is consistent with toluene.

Highly Dispersed Metal Oxide Materials with Inert Carrier Confinement

Example 1

Figure 1:
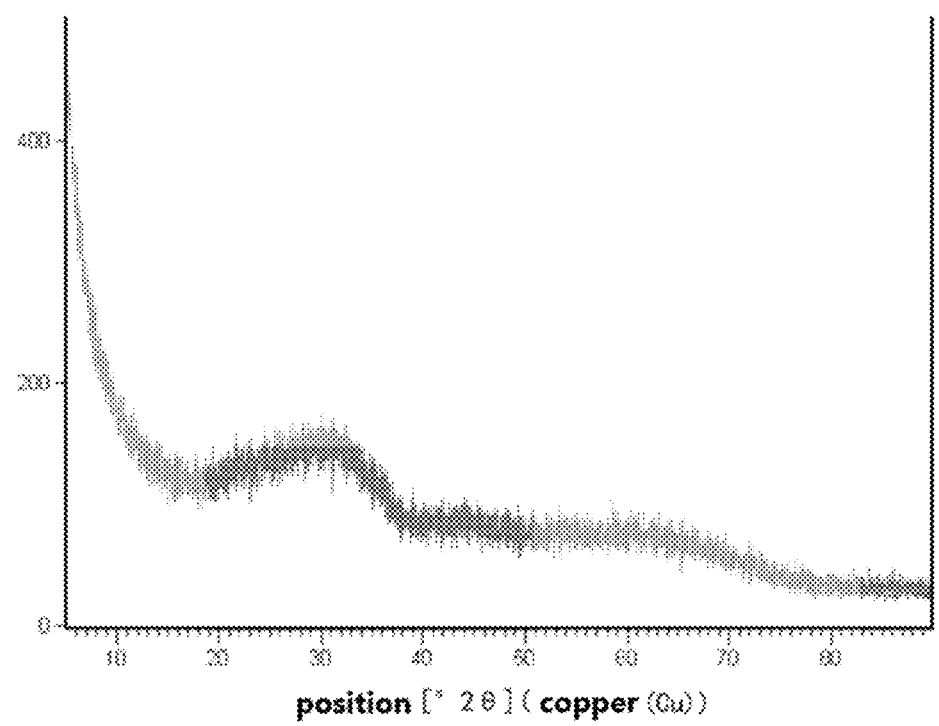
FIG. 1 shows the XRD pattern of material A in Example 1.

1 L of a mixed nitrate aqueous solution containing 0.05 mol/L of $Zn^{2+}$ and 1.0 mol/L of $Al^{3+}$ was prepared, 0.5 mol/L of ammonia solution was added in, the temperature was controlled to be 70° C. and the pH was controlled to be 7.2 simultaneously in the coprecipitation reaction to coprecipitate metal ions. After the reaction, the reaction mixture was aged at 70° C. for 4 h. The precipitate was filtered, washed with deionized water, dried, and calcined at 500° C. for 4 h to obtain a highly dispersed zinc oxide material confined by the inert carrier of alumina, numbered A. A contains zinc in an amount of 8.3% by weight. The XRD pattern is shown in FIG. 1.

Example 2

1 L of a mixed nitrate aqueous solution containing 0.02 mol/L of $Zn^{2+}$, 0.02 mol/L of $Cr^{3+}$ and 1.0 mol/L of $Al^{3+}$ was prepared, with 1.0 mol/L of ammonium carbonate solution added in, and the temperature was controlled to be 70° C. and the pH was controlled to be 7.5 simultaneously in the coprecipitation reaction to coprecipitate metal ions. After the reaction, the reaction mixture was aged at 70° C. for 4 h. The precipitate was filtered, washed with deionized water, dried, and calcined at 500° C. for 4 h to obtain a highly dispersed zinc-chromium oxide material confined by the inert carrier of alumina, numbered B. B contains zinc in an amount of 3.1% by weight and chromium in an amount of 2.5% by weight.

Example 3

1 L of a mixed nitrate aqueous solution containing 0.01 mol/L of $Zn^{2+}$, 0.01 mol/L of $Zr^{4+}$ and 1.0 mol/L of $Al^{3+}$ was prepared, 1.2 mol/L of sodium carbonate solution was added in, the temperature was controlled to be 70° C. and the pH was controlled to be 7.5 simultaneously in the coprecipitation reaction to coprecipitate metal ions. After the reaction, the reaction mixture was aged at 70° C. for 4 h. The precipitate was filtered, washed with deionized water, dried, and calcined at 500° C. for 4 h to obtain a highly dispersed zinc-zirconium oxide material confined by the inert carrier of alumina, numbered C. C contains zinc in an amount of 1.5% by weight and zirconium in an amount of 2.1% by weight.

Example 4

1 L of a mixed nitrate aqueous solution containing 0.01 mol/L of $Zn^{2+}$, 0.02 mol/L of $Cu^{2+}$ and 1.0 mol/L of $Al^{3+}$ was prepared, with 1.5 mol/L of potassium carbonate solution added in, and the temperature was controlled to be 70° C. and the pH was controlled to be 7.9 simultaneously in the coprecipitation reaction to coprecipitate metal ions. After the reaction, the reaction mixture was aged at 70° C. for 4 h. The precipitate was filtered, washed with deionized water, dried, and calcined at 500° C. for 4 h to obtain a highly dispersed zinc-copper oxide material confined by the inert carrier of alumina, numbered D. D contains zinc in an amount of 1.5% by weight and copper in an amount of 3.1% by weight.

Example 5

100 mL of a mixed nitrate aqueous solution containing 0.2 mol/L of $Zn^{2+}$, 0.2 mol/L of $Cr^{3+}$ was prepared, and 100 ml of 1.0 mol/L urea aqueous solution was prepared. The above two solutions were added dropwise into 1 mol of ethyl orthosilicate and reacted for 24 h at room temperature to obtain a gel. The gel was washed with deionized water, dried at 100° C., and calcined at 500° C. for 4 h to obtain a highly dispersed zinc-chromium oxide material confined by the inert carrier of silicon dioxide, numbered E. E contains zinc in an amount of 1.8% by weight and chromium in an amount of 1.5% by weight.

Example 6

100 mL of a mixed nitrate aqueous solution containing 0.2 mol/L of $Zn^{2+}$, 0.2 mol/L of $Zr^{4+}$ was prepared, and 100 ml of 1.0 mol/L urea aqueous solution was prepared. The above two solutions were added dropwise into 1 mol of ethyl orthosilicate and reacted for 24 h at room temperature to obtain a gel. The gel was washed with deionized water, dried at 100° C., and calcined at 500° C. for 4 h to obtain a highly dispersed zinc-zirconium oxide material confined by the inert carrier of silicon oxide, numbered F. F contains zinc in an amount of 1.8% by weight and zirconium in an amount of 2.5% by weight.

Comparative Example 1

Figure 2:
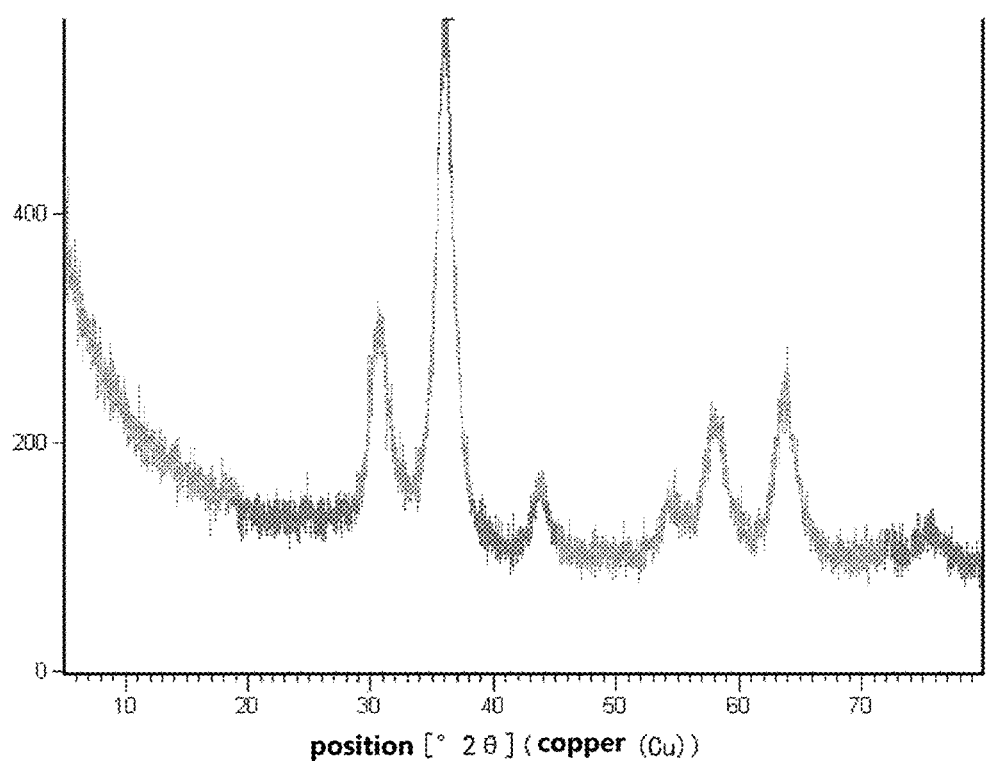
FIG. 2 shows the XRD pattern of the material REF-1 in Comparative Example 1.

100 mL of a mixed nitrate aqueous solution containing 1.0 mol/L of $Zn^{2+}$, 0.50 mol/L of $Cr^{3+}$ and 0.20 mol/L of $Al^{3+}$ was prepared, with 1.0 mol/L of ammonium carbonate solution added in, and the temperature was controlled to be 70° C. and the pH was controlled to be 7.5 simultaneously in the coprecipitation reaction to coprecipitate metal ions. After the reaction, the reaction mixture was aged at 70° C. for 4 h. The precipitate was filtered, washed with deionized water, dried, and calcined at 500° C. for 4 h to obtain a zinc-chromium-aluminum composite oxide, numbered REF-1. The XRD pattern of REF-1 is shown in FIG. 2.

Preparation of Modified Acidic Molecular Sieve

Example 7

The sodium-type ZSM-5 (obtained from catalyst factory of Nankai University) with Si/Al=25 (atomic ratio) was exchanged for 3 times with 0.8 mol/L ammonium nitrate aqueous solution at 80° C. (the volume ratio of ammonium nitrate aqueous solution to molecular sieve was 20:1) to obtain ammonium type ZSM-5 molecular sieve. The ammonium-type ZSM-5 molecular sieve was calcined at 550° C. for 4 h in an air atmosphere, and then immersed in $(NH_4)_2HPO_4$ aqueous solution (content of P in the aqueous solution was 5% by weight) with an equal volume as the ammonium-type ZSM-5 molecular sieve for 24 hours at room temperature, dried, and then calcined at 550° C. for 4 h in an air atmosphere to obtain an acidic ZSM-5 molecular sieve containing 4% of P by weight, numbered G.

Example 8

The sodium-type ZSM-5 (obtained from catalyst factory of Nankai University) with Si/Al=200 (atomic ratio) was exchanged for 3 times with 0.8 mol/L ammonium nitrate aqueous solution at 80° C. (the volume ratio of ammonium nitrate aqueous solution to molecular sieve was 20:1) to obtain ammonium-type ZSM-5 molecular sieve. The ammonium-type ZSM-5 molecular sieve was calcined at 550° C. for 4 h in an air atmosphere, and then immersed in $H_3BO_3$ aqueous solution (content of B in the aqueous solution is 10% by weight) with an equal volume as the ammonium-type ZSM-5 molecular sieve for 24 hours at room temperature, dried, and then calcined at 550° C. for 4 h in an air atmosphere to obtain an acidic ZSM-5 molecular sieve containing 8% of B by weight, numbered H.

Example 9

The sodium-type ZSM-11 (obtained from Aoke company) with Si/Al=40 (atomic ratio) was exchanged for 3 times with 0.8 mol/L ammonium nitrate aqueous solution at 80° C. (the volume ratio of ammonium nitrate aqueous solution to molecular sieve was 20:1) to obtain ammonium-type ZSM-11 molecular sieve. The ammonium-type ZSM-11 molecular sieve was calcined at 550° C. for 4 h in an air atmosphere, and then immersed in $H_3BO_3$ aqueous solution (content of B in the aqueous solution is 10% by weight) with an equal volume as the ammonium-type ZSM-11 molecular sieve for 24 hours at room temperature, dried, and then calcined at 550° C. for 4 h in an air atmosphere to obtain an acidic ZSM-11 molecular sieve containing 8% of B by weight, numbered I.

Example 10

The sodium-type ZSM-5 (obtained from Aoke company) with Si/Al=3 (atomic ratio) was exchanged for 3 times with 0.8 mol/L ammonium nitrate aqueous solution at 80° C. (the volume ratio of ammonium nitrate aqueous solution to molecular sieve was 20:1) to obtain ammonium-type ZSM-5 molecular sieve. The ammonium-type ZSM-5 molecular sieve was calcined at 550° C. for 4 h in an air atmosphere, and then treated with a cyclohexane solution of ethyl orthosilicate (the content of Si in the solution was 10% by weight) at 50° C. for 4 hours. The reaction mixture was evaporated to dryness and calcined at 550° C. for 4 h under an air atmosphere to obtain an acidic ZSM-5 molecular sieve containing 8% of Si by weight (excluding the original Si in the molecular sieve), numbered J.

Example 11

The sodium-type ZSM-5 (obtained from Fuxu Company) with Si/Al=80 (atomic ratio) was exchanged for 3 times with 0.8 mol/L ammonium nitrate aqueous solution at 80° C. (the volume ratio of ammonium nitrate aqueous solution to molecular sieve was 20:1) to obtain ammonium-type ZSM-5 molecular sieve. 500 g of the ammonium-type ZSM-5 molecular sieve was calcined at 550° C. for 4 h in an air atmosphere, and then treated with 1 L/min of nitrogen carrying tetramethylsilane with a volume fraction of 5% at 200° C. for 3 hours. And then calcined at 550° C. for 4h under an air atmosphere to obtain an acidic ZSM-5 molecular sieve containing 2% of Si by weight (excluding the original Si in the molecular sieve), numbered K.

Example 12

The sodium-type ZSM-5 (obtained from catalyst factory of Nankai University) with Si/Al=60 (atomic ratio) was exchanged for 3 times with 0.8 mol/L ammonium nitrate aqueous solution at 80° C. (the volume ratio of ammonium nitrate aqueous solution to molecular sieve was 20:1) to obtain ammonium-type ZSM-5 molecular sieve. The ammonium-type ZSM-5 molecular sieve was calcined at 550° C. for 4 h in an air atmosphere, and then immersed in mixed aqueous solution of magnesium nitrate and cerium nitrate (the content of Mg and Ce in the aqueous solution are 5% and 1.3% by weight, respectively) with an equal volume as the ammonium-type ZSM-5 molecular sieve for 24 hours at room temperature, dried, and then calcined at 550° C. for 4 h in an air atmosphere to obtain an acidic ZSM-5 molecular sieve containing 4% of Me and 1% of Ce by weight, numbered L.

Preparation of Catalyst

Example 13

20 parts by mass of the highly dispersed metal oxide material A confined by the inert carrier from Example 1, 70 parts by mass of acidic molecular sieve G from Example 7, 5 parts by mass of graphite powder, and 5 parts by mass of silicon oxide as a dispersant were mixed uniformly, and then sliced into a columnar catalyst with a diameter of 4 mm and a height of 4 mm using a tablet machine, numbered M. The preparation scheme is summarized in Table 1.

Examples 14-18

The preparation method is similar to Example 13, and the specific scheme is shown in Table 1.

Comparative Example 2

20 parts by mass of the metal composite oxide REF-1 from Comparative Example 1, 70 parts by mass of the acidic molecular sieve G from Example 7, 5 parts by mass of graphite powder, and 5 parts by mass of silicon oxide as a dispersant were uniformly mixed, and then sliced into a columnar catalyst with a diameter of 4 mm and a height of 4 mm using a tablet machine, numbered REF-2.

Example 19

75 parts by mass of the highly dispersed metal oxide material A confined by the inert carrier from Example 1, and 25 parts by mass of the acidic molecular sieve G from Example 7 were uniformly mixed and crushed into a powder of less than 0.05 mm, and then tableted and screened to prepare a granular catalyst with a size in a range of 1-2 mm, numbered S, and the preparation scheme is summarized in Table 1.

Examples 20-24

The preparation method is similar to Example 19, and the specific scheme is shown in Table 1.

Comparative Example 3

75 parts by mass of the metal composite oxide REF-1 from Comparative Example 1 and 25 parts by mass of the acidic molecular sieve G from Example 7 were uniformly mixed and crushed into a powder of less than 0.05 mm, and then tableted and screened to prepare a granular catalyst with a size in a range of 1-2 mm, numbered REF-3.

TABLE 1

| | | preparation scheme for catalyst | | | |
|---|---|---|---|---|---|
| No. of Example | No. of catalyst | No. of highly dispersed metal oxide material confined by inert carrier(by mass %) | No. of modified acidic molecular sieve (by mass %) | Graphite powder (by mass %) | dispersant (by mass %) |
| 13 | M | A (20%) | G (70%) | 5% | silicon oxide (5%) |
| 14 | N | B (30%) | H (55%) | 3% | silicon oxide (12%) |
| 15 | O | C (40%) | I (20%) | 2% | silicon oxide (38%) |
| 16 | P | D (70%) | J (20%) | 5% | silicon oxide (5%) |
| 17 | Q | E (45%) | K (45%) | 2% | silicon oxide (8%) |

TABLE 1-continued preparation scheme for catalyst

| No. of Example | No. of catalyst | No. of highly dispersed metal oxide material confined by inert carrier(by mass %) | No. of modified acidic molecular sieve (by mass %) | Graphite powder (by mass %) | dispersant (by mass %) |
|---|---|---|---|---|---|
| 18 | R | F (60%) | L (25%) | 5% | silicon oxide (10%) |
| 19 | S | A (75%) | G (25%) | 0 | 0 |
| 20 | T | B (10%) | H (90%) | 0 | 0 |
| 21 | U | C (90%) | I (10%) | 0 | 0 |
| 22 | V | D (50%) | J (50%) | 0 | 0 |
| 23 | W | E (80%) | K (20%) | 0 | 0 |
| 24 | X | F (65%) | L (35%) | 0 | 0 |

Performance Test of Catalyst

Example 25

200 g of the catalyst M was loaded into a stainless steel reaction tube with an inner diameter of 28 mm, and activated with 1000 ml/min of hydrogen at 300° C. for 4 h. Then the hydrogen flow was switched to a synthetic gas flow and toluene flow was introduced, a reaction was carried out under the following conditions: reaction temperature (T)=400° C., reaction pressure (P)=7.0 MPa, gas volume space velocity (GHSV) under standard conditions=6000 $h^{-1}$, the volume ratio of CO to $H_2$ in the synthetic gas was 1:1, mass space velocity (WHSV) of toluene =1.0 $h^{-1}$ After the reaction had stabilized, the product was analyzed by gas chromatography. The reaction results are shown in Table 2.

Examples 26-30

Example 25 was repeated, but the catalyst M in Example 25 was replaced with the catalyst N-R. The reaction results are shown in Table 2.

Comparative Example 4

Example 25 was repeated, but the catalyst M in Example 25 was replaced with the catalyst REF-2. The reaction results are shown in Table 2.

TABLE 2

Catalytic reaction results in Examples 25-30 and Comparative Example 4

| | Catalyst | Conversion rate of carbon monoxide (%) | Conversion rate of toluene (%) | Selectivity to xylene (%) | Ratio of P-xylene (%) |
|---|---|---|---|---|---|
| Example 25 | M | 34.5 | 28.5 | 93.6 | 98.5 |
| Example 26 | N | 36.1 | 27.1 | 88.9 | 97.6 |
| Example 27 | O | 30.3 | 20.3 | 86.0 | 94.1 |
| Example 28 | P | 24.4 | 21.7 | 90.0 | 97.3 |
| Example 29 | Q | 27.7 | 22.9 | 90.9 | 98.2 |
| Example 30 | R | 26.3 | 22.5 | 92.1 | 93.8 |
| Comparative Example 4 | REF-2 | 8.2 | 14.9 | 42.0 | 94.0 |

Example 31

5 g of the catalyst S was loaded into a stainless steel reaction tube with an inner diameter of 8 mm, and activated with 50 ml/min of hydrogen at 300° C. for 4 h. Then the hydrogen flow was switched to a synthetic gas flow and toluene flow was introduced, a reaction was carried out under the following conditions: reaction temperature (T)=400° C., reaction pressure (P)=4.0 MPa, gas volume space velocity (GHSV) under standard conditions=4000 $h^{-1}$, the volume ratio of CO to $H_2$ in the synthetic gas was 1.5:1, mass space velocity (WHSV) of toluene=0.5$^{-1}$. After 500 h of the reaction, the products were analyzed by gas chromatography. The reaction results are shown in Table 3.

Examples 32-36

Reaction conditions and reaction results are shown in Table 3. Other operations were the same as in Example 31.

Comparative Example 5

5 g of catalyst REF-3 was placed in a stainless steel reaction tube with an inner diameter of 8 mm, and activated with 50 ml/min hydrogen at 300° C. for 4 h, a reaction was carried out under the following conditions: reaction temperature (T)=400° C., reaction pressure (P)=4.0 MPa, the volumetric space velocity of synthetic gas (GHSV) under standard conditions=4000 $h^{-1}$, the volume fraction of hydrogen in the synthetic gas (mixed gas of CO and $H_2$) V ($H_2$)%=40%, mass space velocity (WHSV) of toluene=0.5 $h^{-1}$. After 500 h of reaction, the products were analyzed by gas chromatography. The reaction results are shown in Table 3.

TABLE 3

Catalytic reaction results in Examples 31-36 and Comparative Example 5

| | Catalyst | reaction condition | Conversion rate of carbon monoxide (%) | Conversion rate of toluene (%) | Selectivity to xylene (%) | Ratio of P-xylene (%) |
|---|---|---|---|---|---|---|
| Example 31 | S | T = 400° C.; P = 4.0 MPa; WHSV = 0.5 h$^{-1}$; GHSV = 4000 h$^{-1}$; V(H$_2$) % = 40% | 25.8 | 78.2 | 87.8 | 98.8 |
| Example 32 | T | T = 370° C.; P = 10.0 MPa; WHSV = 0.01 h$^{-1}$; GHSV = 20000 h$^{-1}$; V(H$_2$) % = 90% | 57.9 | 100 | 93.9 | 97.9 |
| Example 33 | U | T = 300° C.; P = 0.5 MPa; WHSV h$^{-1}$; GHSV = 1000 h$^{-1}$; V(H$_2$) % = 10% | 12.2 | 15.5 | 82.0 | 94.3 |
| Example 34 | V | T = 450° C.; P = 3.0 MPa; WHSV = 20 h$^{-1}$; GHSV = 8000 h$^{-1}$; V(H$_2$) % = 65% | 50.3 | 8.4 | 98.2 | 99.3 |
| Example 35 | W | T = 390° C.; P = 5.0 MPa; WHSV = 2 h$^{-1}$; GHSV = 7000 h$^{-1}$; V(H$_2$) % = 30% | 31.3 | 29.7 | 96.0 | 98.8 |
| Example 36 | X | T = 340° C.; P = 7.0 MPa; WHSV = 1 h$^{-1}$; GHSV = 12000 h$^{-1}$; V(H$_2$) % = 75% | 26.9 | 52.5 | 83.6 | 92.8 |
| Comparative Example 5 | REF-3 | T = 400° C.; P = 4.0 MPa; WHSV = 0.5 h$^{-1}$; GHSV = 4000 h$^{-1}$; V(H$_2$) % = 40% | 8.9 | 17.9 | 45.0 | 95.0 |

Regeneration Performance Test of Catalyst

Example 37

The deactivated catalyst in Example 25 was treated with a mixture of 2 vol % oxygen and 98 vol % nitrogen at 550° C. for 10 h to regenerate the catalyst for one round. It was then reacted under the conditions of Example 25. A total of five rounds of regeneration were performed in the same way. The catalytic activity data after 500 h of reaction for each round were selected for comparison. The results are shown in Table 4.

TABLE 4

Test results of regeneration performance of catalyst in Example 37

| Regeneration times | Conversion rate of carbon monoxide (%) | Conversion rate of toluene (%) | Selectivity to xylene (%) | Ratio of P-xylene (%) | Life of each round (h) |
|---|---|---|---|---|---|
| 1 | 35.4 | 28.9 | 94.2 | 98.3 | 3300 |
| 2 | 34.1 | 28.1 | 93.3 | 98.0 | 3400 |
| 3 | 32.2 | 27.4 | 93.5 | 96.9 | 3200 |
| 4 | 29.5 | 27.1 | 93.6 | 97.3 | 3500 |
| 5 | 30.5 | 26.9 | 94.0 | 96.9 | 3200 |

Example 38

The deactivated catalyst in Example 31 was treated with a mixture of 2 vol % oxygen and 98 vol % nitrogen at 550° C. for 10 h to regenerate the catalyst for one round. It was then reacted under the conditions of Example 31. A total of five rounds of regeneration were performed in the same way. The catalytic activity data after 500 h of reaction for each round were selected for comparison. The results are shown in Table 5.

TABLE 5

Test results of regeneration performance of catalyst in Example 38

| Regeneration times | Conversion rate of carbon monoxide (%) | Conversion rate of toluene (%) | Selectivity to xylene (%) | Ratio of P-xylene (%) | Life of each round (h) |
|---|---|---|---|---|---|
| 1 | 25.4 | 77.9 | 85.1 | 97.7 | 3200 |
| 2 | 25.9 | 77.7 | 86.4 | 98.2 | 3300 |
| 3 | 25.1 | 78.0 | 85.3 | 96.8 | 3100 |
| 4 | 25.5 | 77.1 | 85.4 | 97.1 | 3400 |
| 5 | 25.7 | 76.9 | 83.7 | 96.8 | 3100 |

Examples 39-44

Example 25 was repeated, but the raw material of toluene was replaced with other aromatic hydrocarbon. The reaction results are shown in Table 6.

TABLE 6

Catalytic reaction results

| No. of Example | raw material of aromatic hydrocarbon | Conversion rate of carbon monoxide (%) | Conversion rate of aromatic hydrocarbon (%) | Selectivity to xylene (%) | Ratio of P-xylene (%) |
|---|---|---|---|---|---|
| 39 | benzene | 25.1 | 90.1 | 65.2 | 97.4 |
| 40 | ethylbenzene | 26.0 | 88.8 | 70.1 | 96.5 |
| 41 | isopropylbenzene | 24.1 | 67.1 | 58.9 | 95.2 |
| 42 | sym-trimethylbenzene | 24.3 | 66.6 | 71.3 | 94.8 |
| 43 | sym-tetramethylbenzene | 21.7 | 64.3 | 65.1 | 95.5 |
| 44 | biphenyl | 20.4 | 85.7 | 75.3 | 94.6 |

The above is only a few embodiments of the present invention, and does not limit the present invention in any form. Although the present invention is disclosed in the above preferred embodiments, it is not intended to limit the present invention. Without departing from the scope of the technical solutions of the present invention, slight changes or modifications according to the technical content disclosed above by anyone skilled in the art are equivalent to equivalent implementation cases and all fall within the scope of the technical solutions.

The invention claimed is:

1. A method for directly preparing p-xylene from synthetic gas and an aromatic hydrocarbon, comprising:

contacting a feedstock containing synthetic gas and an aromatic hydrocarbon excluding p-xylene with a catalyst in a reaction zone under reaction conditions sufficient to convert at least part of the feedstock to obtain a reaction effluent containing p-xylene; and separating p-xylene from the reaction effluent, wherein the catalyst comprises a metal oxide material confined by an inert carrier, an acidic molecular sieve, and at least one selected from graphite powder and dispersant;

wherein the inert carrier is at least one selected from silicon oxide and alumina;

wherein the content of the metal oxide material in terms of metal is less than or equal to 10% by mass calculated based on the weight of the metal oxide material confined by the inert carrier; and wherein the acidic molecular sieve is a modified acidic molecular sieve selected from the group consisting of modified acidic ZSM-5 molecular sieve, modified acidic ZSM-11 molecular sieve and mixtures thereof.

2. The method according to claim 1, further comprising at least one of:

the reaction zone comprises a fixed bed reactor, or multiple fixed bed reactors in series and/or parallel;

the reaction conditions comprise: a reaction temperature in a range of 300° C. to 450° C., a reaction pressure in a range of 0.5 MPa to 10.0 MPa, a molar ratio of hydrogen to carbon monoxide in the synthetic gas in a range of 1:9 to 9:1, a weight hourly space velocity of aromatic hydrocarbon in a range of 0.01 $h^{-1}$ to 20 $h^{-1}$, and a volume hourly space velocity of synthetic gas in the standard state in a range of $1000^{-1}$ to 20000 $h^{-1}$;

the metal oxide material is an oxide of at least one of zinc, chromium, zirconium, copper, manganese, platinum and palladium;

the content of the metal oxide material in terms of metal in the metal oxide material confined by the inert carrier is less than or equal to 5% by weight calculated based on the weight of the metal oxide material confined by the inert carrier;

the particle size of the metal oxide material in the metal oxide material confined by the inert carrier is less than or equal to 100 nm;

the modified acidic molecular sieve is provided by modifying acidic ZSM-5 molecular sieve or acidic ZSM-11 molecular sieve, wherein the modification is one or more of modification by phosphorus, modification by boron, modification by silicon, modification by an alkaline earth metal, and modification by a rare earth metal;

the atomic ratio of silicon to aluminum (Si/Al) in the modified acidic ZSM-5 and ZSM-11 molecular sieves is 3 to 200;

the particle shape of the catalyst is spherical, bar-shaped, cylindrical, semi-cylindrical, prismatic, clover-shaped, ring-shaped, pellet-shaped, regular or irregular particle-shape or flake; and the aromatic hydrocarbon excluding p-xylene is at least one aromatic hydrocarbon having the following general formula:

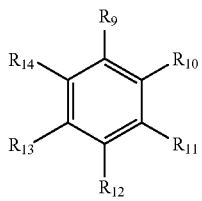

wherein, $R_9$, $R_{10}$, $R_{11}$, $R_{12}$, $R_{13}$ and $R_{14}$ are each independently selected from hydrogen, or a $C_1$-$C_{10}$ hydrocarbyl.

3. The method according to claim 1, wherein the catalyst comprises the metal oxide material confined by the inert carrier in an amount ranging from 10% to 90% by weight, the acidic molecular sieve in an amount ranging from 10% to 90% by weight, the graphite powder in an amount ranging from 0% to 10% by weight and the dispersant in an amount ranging from 0% to 40% by weight;

wherein the total content of the metal oxide material confined by the inert carrier and the acidic molecular sieve is in a range of 60% to 100% by weight; and wherein the weight percentage is calculated based on the total weight of the catalyst.

4. The method according to claim 1, wherein the catalyst comprises the metal oxide material confined by the inert carrier in an amount ranging from 20% to 80% by weight, the acidic molecular sieve in an amount ranging from 20% to 80% by weight, the graphite powder in an amount ranging from 0% to 5% by weight and the dispersant in an amount ranging from 0% to 30% by weight; and wherein the weight percentage is calculated based on the total weight of the catalyst.

5. The method according to claim 1, wherein the average particle size of the metal oxide material confined by the inert carrier is less than or equal to 5 mm, and the average particle size of the acidic molecular sieve particles is less than or equal to 5 mm.

6. The method according to claim 1, wherein the catalyst is prepared by a method comprising the following steps:
(1) providing a metal oxide material confined by the inert carrier;
(2) providing a modified acidic molecular sieve;
(3) mixing the metal oxide material confined by the inert carrier obtained in step
(1) with the modified acidic molecular sieve obtained in step (2) and at least one selected from graphite powder and dispersant to obtain a mixture, and molding the mixture.

7. The method according to claim 6, the method for preparing the catalyst further comprising at least one of the following features:
in step (1), the metal oxide material confined by the inert carrier is prepared by a precipitation-calcination method, or by a sol-gel method;
the modified acidic molecule is one selected from the group consisting of phosphorus-modified, boron-modified, silicon-modified, alkaline earth metal-modified and/or rare earth metal-modified ZSM-5 molecular sieve, and phosphorus-modified, boron-modified, silicon-modified, alkaline earth metal-modified and/or rare earth metal-modified ZSM-11 molecular sieve; and in step (3), the mixture is molded into catalyst particles by an extrusion method or a molding method.

8. The method according to claim 6, wherein in step (1) of the method for preparing the catalyst, the metal oxide material confined by the inert carrier is provided by a method comprising the steps as follows:
formulating a mixed metal salt aqueous solution from a catalytically active metal salt and an aluminum salt;
contacting the mixed metal salt aqueous solution with a precipitant aqueous solution to co-precipitate the metal ions in the mixed metal salt aqueous solution;
aging the solution mixture; and
washing, drying and calcining the precipitate to obtain the metal oxide material confined by the inert carrier.

9. The method according to claim 8, further comprising at least one of the following features:
the catalytically active metal salt and aluminum salt are one selected from hydrochloride, sulfate and nitrate;
the precipitant aqueous solution is one selected from sodium carbonate, potassium carbonate, ammonium carbonate, sodium bicarbonate, potassium bicarbonate, ammonium bicarbonate, ammonia water, sodium hydroxide, potassium hydroxide and mixtures thereof;
the co-precipitation is carried out at a temperature in a range of 0° C. to 90° C.;
the pH value during the co-precipitation is in a range of 7.0 to 8.5;
the time for aging is not less than 1 hour; and
the calcination is carried out at a temperature in a range of 300° C. to 700° C.

10. The method according to claim 6, wherein in step (1) of the method for preparing the catalyst, the metal oxide material confined by the inert carrier is provided by
a method comprising the steps:
adding an aqueous solution of a catalytically active metal salt and an aqueous solution of a precipitant together into siloxane-based compound, so that a co-precipitation and sol-gel reaction can be carried out, and then washing, drying and then calcining the obtained gel to prepare the metal oxide material confined by the inert carrier.

11. The method according to claim 10, wherein the precipitant comprises ammonium carbonate, ammonia water, ammonium bicarbonate, ammonium dihydrogen carbonate, urea and mixtures thereof; the siloxane-based compound is an alkyl orthosilicate, preferably selected from methyl orthosilicate, ethyl orthosilicate, n-propyl orthosilicate, isopropyl orthosilicate, tetrabutyl orthosilicate, isobutyl orthosilicate, tert-butyl orthosilicate or mixtures thereof.

12. The method according to claim 1, wherein the aromatic hydrocarbon excluding p-xylene comprises benzene, toluene, ethylbenzene, m-xylene, o-xylene, cumene, sym-trimethylbenzene, sym-tetramethylbenzene, biphenyl and mixtures thereof.

13. The method according to claim 1, wherein the reaction conditions comprise: a reaction temperature in a range of 320° C. to 400° C., a reaction pressure in a range of 5.0 MPa to 10.0 MPa, a molar ratio of hydrogen to carbon monoxide in the synthetic gas in a range of 1:9 to 1:1, a mass space velocity of aromatic hydrocarbon in a range of 0.5 $h^{-1}$ to 3 $h^{-1}$, and a volumetric space velocity of synthetic gas in a range of 1000 $h^{-1}$ to 4000 $h^{-1}$.

* * * * *